United States Patent [19]

Bujan et al.

[11] 4,382,453
[45] May 10, 1983

[54] FLOW RISTRICTOR FOR FLEXIBLE TUBING

[75] Inventors: Albert F. Bujan, Waukegan; Paul L. Pluta, Highland Park, both of Ill.

[73] Assignee: Abbott Laboratories, North Chicago, Ill.

[21] Appl. No.: 270,776

[22] Filed: Jun. 4, 1981

Related U.S. Application Data

[63] Continuation-in-part of Ser. No. 52,387, Jun. 27, 1979, abandoned.

[51] Int. Cl.³ .............................................. F16K 7/04
[52] U.S. Cl. ................................ 138/40; 24/255 SL; 128/346; 251/10; 604/250
[58] Field of Search ..................... 138/40, 44, 45, 103, 138/119; 128/346, 214 R, 214 C, 213; D24/27; 24/255 SL; 251/4, 9, 10

[56] References Cited

U.S. PATENT DOCUMENTS

| | | | |
|---|---|---|---|
| D. 234,204 | 1/1975 | Miller | 24/255 SL |
| 2,563,236 | 8/1951 | Gragg | 24/248 R |
| 2,855,173 | 10/1958 | Treptow | 251/4 |
| 3,042,067 | 7/1962 | Hidding | 137/315 |
| 3,061,263 | 10/1962 | Butler | 251/9 |
| 3,102,710 | 9/1963 | Dresden | 251/9 |
| 3,204,636 | 9/1965 | Kariher et al. | 251/4 |
| 3,335,753 | 8/1967 | Kiser | 251/9 |
| 3,497,175 | 2/1970 | Koland | 251/9 |
| 3,713,622 | 1/1973 | Dinger | 24/255 SL |
| 3,825,012 | 7/1974 | Nicoll | 251/9 |
| 3,874,042 | 4/1975 | Eddleman et al. | 24/255 SL |
| 4,272,051 | 6/1981 | Huggins | 251/9 |

Primary Examiner—John W. Shepperd
Attorney, Agent, or Firm—Neil E. Hamilton; Robert L. Niblack

[57] ABSTRACT

A flow control device which will limit the maximum flow rate of liquid through a length of flexible tubing such as utilized in a parenteral administration set so as to prevent a runaway condition. A base and a cover member are provided which are hingedly attached to each other and have a groove for the placement of the tubing therein. The groove or grooves are of a dimension such that when the tubing is seated therein and the cover and base members brought together, the tubing is prevented from expanding beyond a predetermined dimension. Frictional engaging means are provided on the base and the cover member so as to provide a temporary closing of the cover and base members over the tubing.

8 Claims, 9 Drawing Figures

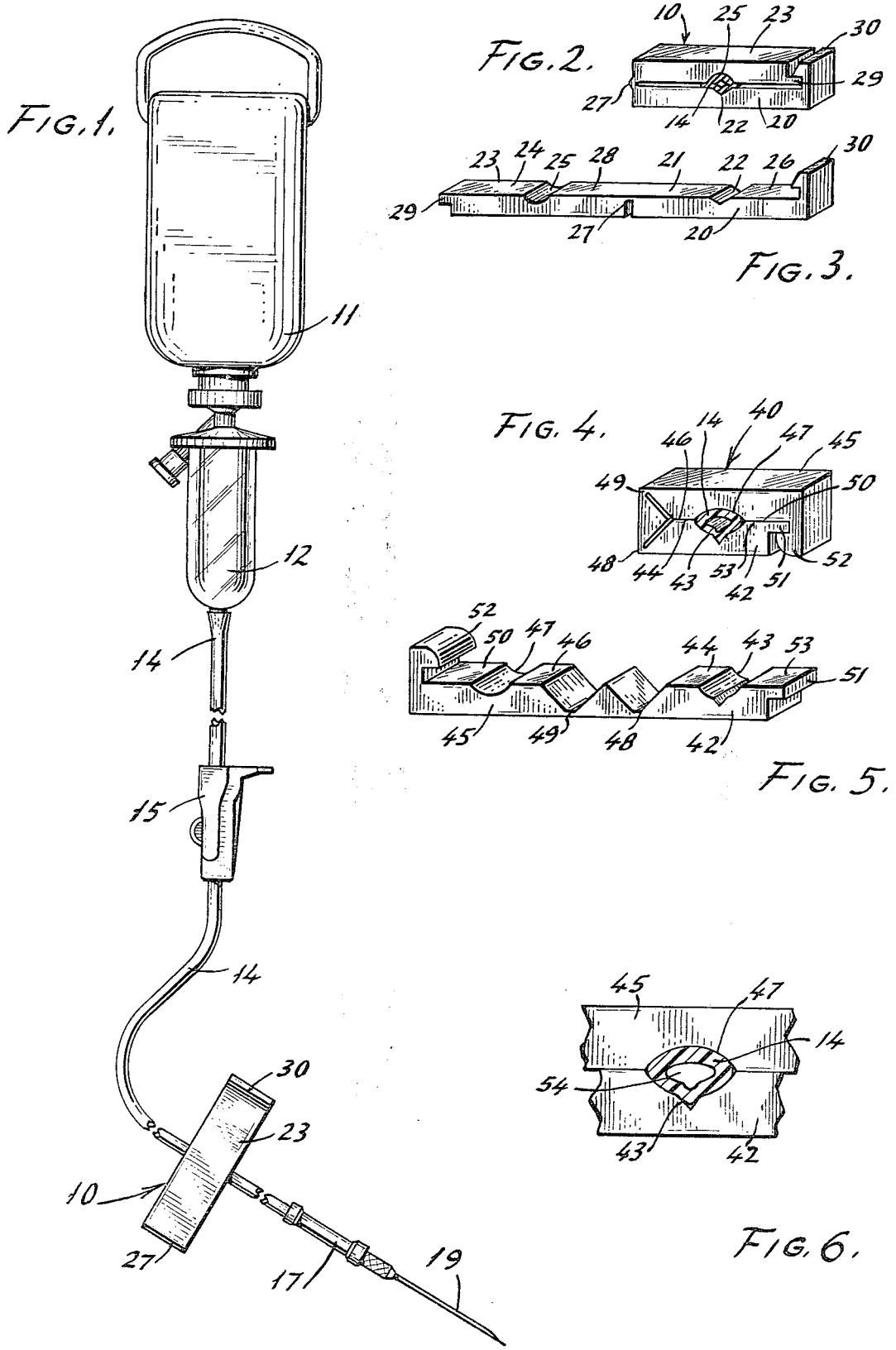

FLOW RISTRICTOR FOR FLEXIBLE TUBING

CROSS REFERENCE TO RELATED APPLICATION

This application is a continuation-in-part of U.S. Ser. No. 52,387, filed June 27, 1979, now abandoned.

BACKGROUND OF THE INVENTION

This invention relates to a simplified flow control device which will prevent the flow of fluid through a length of flexible tubing exceeding a predetermined amount. More particularly, this invention relates to a flow control device having stationary components for use with flexible tubing in a parenteral administration set. The flow control device is constructed with a base and cover having a channel or groove of a predetermined dimension to accommodate the tubing and prevent it from exceeding a predetermined flow rate.

Flow control devices of a rather simplified construction are described in U.S. Pat. Nos. 2,855,173; 3,042,067; 3,061,263 and 3,497,175. While these particular clamping devices are rather basic in their construction, they are designed to control the flow of liquid in varying degrees as well as to completely shut off flow in flexible tubing. There is not currently available a flow control device which is constructed solely for the purpose of preventing excessive flow through a length of flexible tubing. In some instances there occurs during the administration of I.V. fluids a "runaway" condition wherein the flow of liquid is no longer under the influence of a flow control device such as a clamp. This can happen should a clamp become disengaged from the tubing or the tubing cold flow under the force of the clamp. In some instances this condition could be serious to a recipient in that an excessive amount of liquid would be delivered into the vein. To prevent such a condition from occurring, the present invention affords a simplified unit which will surround the tubing and prevent it from expanding beyond the predetermined position to thereby control the flow of fluid therethrough.

It is an advantage of the present invention to provide a flow control device which will prevent the flow of fluid through flexible tubing exceeding a predetermined amount. Other advantages are a flow control unit which is disposable, can be molded in a unitary manner, can be positioned over the flexible tubing in a fast and efficient manner, with a single hand operation and can be fabricated without expensive molding procedures and from various plastic materials.

SUMMARY OF THE INVENTION

The foregoing advantages are accomplished and the shortcomings of the prior art are overcome by the present flow restrictor device which has a base member providing a first indentation for placement of a portion of a length of tubing therein. A cover member is hingedly attached to the base member and provides a second indentation or projection for orientation with the first indentation and for surrounding or contacting the tubing. The hinging section interconnects the base and cover members at one end thereof and frictional engaging means are provided at the opposing ends of the cover and base so as to temporarily secure the cover and base members together with the indentations surrounding the tubing. In a preferred manner, the flow restrictor device is molded in a unitary structure with a plurality of grooves extending across a block member. At least one hinging section is provided by one of the grooves connecting the cover and the base and frictional engaging means are provided by means of a flanged portion for engagement with an opposing latch portion. A groove or indentation is provided in the base or cover members for holding the tubing therein. Preferably, aligned grooves will be provided in both the cover and base members or a projection in one of said members and a groove in the other.

BRIEF DESCRIPTION OF THE DRAWING

A better understanding of the flow restrictor device of the present invention will be accomplished by reference to the drawing wherein:

FIG. 1 is a view in side elevation illustrating the flow restrictor unit operatively associated with a parenteral administration set.

FIG. 2 is a perspective view of one embodiment of this invention illustrating the flow control unit engaging a section of flexible tubing.

FIG. 3 is a perspective view of the flow control unit shown in FIG. 2 after molding and prior to assembly.

FIG. 4 is a view similar to FIG. 2 showing another embodiment of this invention.

FIG. 5 is a view of the flow control unit shown in FIG. 4 after molding and prior to engagement over a length of tubing.

FIG. 6 is a detailed view of the flow control unit shown in FIG. 4 illustrating the compression and holding of the tubing.

DESCRIPTION OF THE PREFERRED EMBODIMENT

Figure 7:
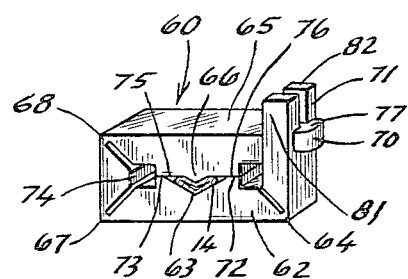
FIG. 7 is a perspective view of still another embodiment of this invention.

Proceeding to a detailed description of one preferred embodiment of this invention, the flow control unit, generally 10, is shown for use in conjunction with a parenteral administration set composed of a solution container 11 and a drip chamber 12 which is interconnected to a hypodermic needle 19 by means of tubing 14 and needle adapter 17.

As best shown in FIGS. 2 and 3, flow restrictor device 10 has a base member 20 with flat sections 21 and 26 and a V-shaped indentation 22 therebetween. Attached to base member 20 is a cover member 23 which is integrally secured to base member 20 by means of a hinge section 27. Cover member 23 also has an indentation 25 surrounded by flat sections 24 and 28. It will be noted that indentation 25 has a rounded or curved configuration. Extending from cover member 23 is a flange portion 29 and at the opposite end of restrictor device 10, as viewed in FIG. 3, is an upwardly extending latch portion 30. As will be explained later, flow restrictor unit 10 is fabricated so that when it is in an assembled condition as shown in FIG. 2, flange portion 29 will engage latch portion 30 in an integral snap-fit manner so as to be frictionally retained therein. Indentations or channels 22 and 25 are positioned in base 20 and cover 23, respectively, so that they are orientated with each other when the base member 20 and cover member 23 are in a closed position.

FIGS. 4, 5 and 6 illustrate another embodiment in restrictor device 40 which differs from restrictor unit device 10 in that it has two hinge or groove sections 48 and 49 interconnecting a base member 42 and cover member 45 with parallel axes. A V-shaped indentation 43 is disposed in base member 42 surrounded by flat sections 44 and 53. Similarly, in cover member 45 there is a rounded indentation 47 surrounded by flat sections 50 and 46. Referring specifically to FIG. 5, it will be noted that when tubing 14 is compressed and restricted in indentations 43 and 47 it will assume somewhat the same configuration as the indentations resulting in lumen 54. As viewed in FIG. 6, a latch portion 52 extends upwardly from cover member 45. At the opposing end of restrictor device 40 there is a flange portion 51 for engagement with latch portion 52 when the unit 40 is in an assembled condition as shown in FIG. 4 and the channels 43 and 47 orientated around tubing 14.

Figure 9:
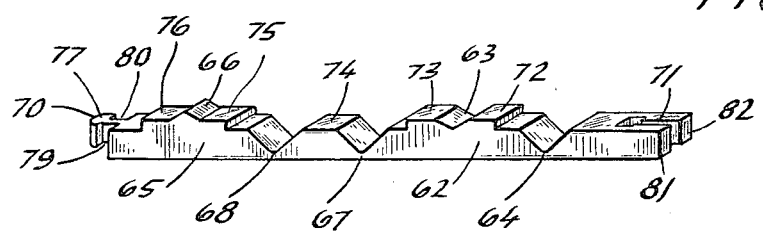
FIG. 9 is a view similar to FIGS. 3 and 5 except of the flow control unit shown in FIG. 7.
Figure 8:
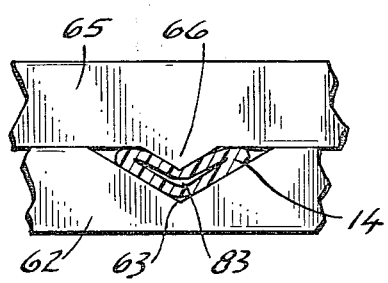
FIG. 8 is a detailed view of the flow control unit shown in FIG. 7 showing the restriction of the tubing therein.

Flow restrictor device 60 as illustrated in FIGS. 7, 8 and 9 differs from the previous embodiments in that it has three hinge sections 64, 67 and 68 as well as a projection 66. Hinge section 64 provides a hinging movement for latch portion 71 to extend upwardly from base member 62. Base member 62 has a V-shaped indentation 63 surrounded by flat sections 72 and 73. A V-shaped projection 66 is disposed in cover member 65 which is bordered by flat sections 75 and 76. A flat section 74 is also disposed between hinge sections 67 and 68. Extending from cover member 65 and at the end of unit 60 opposite base member 62 is a flange portion 70 which in this instance has a rounded head member 77 with opposing slots 79 and 80. Restrictor device 60 is constructed so that when it is in an assembled condition, slots 79 and 80 will accommodate leg portions 81 and 82 of latch portion 71 in a snap fit arrangement, with head 77 projecting therefrom as seen in FIG. 7. Channel 63 is disposed in base 62 and projection 66 in cover 65, respectively, so as to be orientated with each other as well as surround and contact tubing 14 when in an assembled or latched condition. As best seen in FIG. 8, when tubing 14 is compressively restricted in groove 63 by projection 66 it will result in having a single lumen 83.

Operation

A better understanding of the advantages of flow restrictor devices 10, 40 and 60 will be had by a description of their operation. Referring to flow restrictor device 10 first, it will be injection molded from a polyolefin rigid plastic material and will appear as illustrated in FIG. 3 as it comes from the mold. To assemble unit 10 on an I.V. set as shown in FIG. 1, all that is required is to position channel 22 with the tubing 14 thereover and to move cover member 23 over base member 20 by means of hinge section 27 so that flange portion 29 will fit in latch portion 30. The unit will then appear as in FIG. 2 with the tubing seated in channels 22 and 25. These channels will be dimensioned so as to slightly contact tubing 14 and to compress it to a predetermined amount. The amount of compression will be determined by the amount of maximum flow through tubing 14. Unit 10 will then be shipped with the I.V. set as shown in FIG. 1. The administration set will be utilized in the usual manner with a venipuncture made by means of hypodermic needle 19 and the flow of liquid through tubing 14 from I.V. solution container 11 controlled by means of clamp 15. In the event clamp 15 should become disengaged from tubing 14 or the compression of the tubing be such that the tubing will assume a cold-flow condition such that an excessive amount of fluid will flow through tubing 14, this flow will be limited and will not attain a flow rate above that determined by flow control unit 10. This is accomplished by means of the confinement of tubing 14 in channels 22 and 25. A potentially undesired runaway condition is thereby avoided by means of flow control unit 10. It should be pointed out that the restrictive compression of tubing 14 in grooves 22 and 24 will be the same as in unit 40 and illustrated in FIG. 5 with the double lumen 54, 55 being formed.

The fabrication and use of flow control units 40 and 60 will be basically the same as described in flow control unit 10. The basic difference in unit 40 is in its assembly in that a double hinging action will be afforded during assembly by means of hinging sections 48 and 49. The advantage of this unit over that shown in unit 10 is that a more positive contact is afforded between base member 42 and cover member 45 by means of flat sections 44 and 53 surrounding channel 43 and contact by flat sections 50 and 46 in cover member 45 engaging the flat sections 53 and 44, respectively, to positively retain tubing 14 in channels or indentations 47 and 43. A multiple hinging action is also provided in unit 60 which also, when in an assembled condition and surrounding tubing 14 will provide contact between flat sections 72 and 73 of base member 62 and flat sections 76 and 75, respectively, of cover member 65 so as to positively confine tubing 14 in indentation 63 by projection 66. Unit 60 further provides the advantage of easier placement on the tubing, more positive locking and easier release.

Flow restrictor units 10, 40 and 60 as previously indicated are molded from a polyolefin plastic material. These units can be molded from such plastic materials as nylon, ABS, and the like. It will also be seen that the channels or indentations such as 22 in base member 20 are formed in a V-shaped configuration while the channels or indentations 25 in cover 23 are formed in a curved configuration or in the form of a projection 66. This offers the advantage of preforming the tubing in its more natural oval form and effecting a lumen of predetermined and constant size during the flow of fluid therethrough. If desired, these channels or projections could be formed in either the disclosed base or cover members.

It will thus be seen that through the present invention there is now provided a flow control unit which will avoid an undesired runaway condition in an I.V. administration set. The flow control units are easily fabricated and assembled so as to not add substantial additional cost to the I.V. set. Further, if for any reason the flow restrictor units are not desired they can be removed from the set without undue manipulation.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

We claim:

1. A flow restrictor device for controlling fluid flow through a length of flexible tubing comprising:
   a base member;
   a cover member;

hinging means interconnecting said base and cover members at one end of said members; and frictional engaging means cooperatively associated with the other ends of said members to retentively hold said base and cover members in a face-to-face relationship;

said base member and said cover member defining oppositely positioned indentations for placement of tubing therebetween with at least one of said indentations constructed and arranged to provide lumen controlling expansion of said tubing as well as a constant size;

said base member and said cover member further defining flat sections adjacent said indentations;

so that when said length of tubing is positioned in said indentations and said cover and base members are held together by said engaging means, said flat sections will engage and said tubing will be contacted by said cover and base members to a predetermined degree and expansion of said tubing is controlled in a limited manner by said indentations to provide a lumen of constant size during the flow of fluid therethrough.

2. The flow restrictor device as defined in claim 1 wherein said hinging means comprises a single hinging member.

3. The flow restrictor device as defined in claim 1 wherein said frictional engaging means is defined by a flanged portion and a latch portion extending from said cover or base members.

4. A flow restrictor device for controlling fluid flow through a length of flexible tubing comprising:

a base member;

a cover member;

hinging means interconnecting said base and cover members at one end of said members; and frictional engaging means cooperatively associated with the other ends of said members to retentively hold said base and cover members in a face-to-face relationship;

said base member and said cover member defining an oppositely positioned projection and indentation for placement of tubing therebetween said indentation constructed and arranged to provide lumen controlling expansion of said tubing as well as constant size;

said base member and said cover member further defining flat sections adjacent said projection and indentation;

so that when said length of tubing is positioned in said indentation and said cover and base members are held together by said engaging means, said flat sections will engage and said tubing will be contacted by said cover and base members to a predetermined degree and expansion of said tubing is controlled in a limited manner by said projection and indentation to provide a lumen of constant size during the flow of fluid therethrough.

5. The flow restrictor device as defined in claim 4 wherein said frictional engaging means is defined by a slotted head portion and a latch portion for snap fitment with said slotted head portion.

6. The flow restrictor device as defined in claims 1 or 4 wherein said base and cover members and said hinging and engaging means are all formed as a unitary structure.

7. The flow restrictor device as defined in claims 1 or 4 wherein said hinging means comprises two hinging portions with parallel axes.

8. The flow restrictor device is defined in claims 1 or 4 wherein said indentations providing lumen controlling expansion and constant size tubing are substantially V-shaped in configuration.

* * * * *

UNITED STATES PATENT AND TRADEMARK OFFICE
CERTIFICATE OF CORRECTION

PATENT NO. : 4,382,453
DATED : May 10, 1983
INVENTOR(S) : Albert F. Bujan; Paul L. Pluta It is certified that error appears in the above—identified patent and that said Letters Patent is hereby corrected as shown below:

The title should be corrected to read:

-- FLOW RESTRICTOR FOR FLEXIBLE TUBING --.

Signed and Sealed this

Twenty-eighth Day of June 1983

[SEAL]

Attest:

GERALD J. MOSSINGHOFF

Attesting Officer       Commissioner of Patents and Trademarks